(12) United States Patent
Cheng

(10) Patent No.: US 7,799,804 B2
(45) Date of Patent: *Sep. 21, 2010

(54) THERAPEUTIC AGENTS

(75) Inventor: Leifeng Cheng, Mölndal (SE)

(73) Assignee: Astrazeneca AB, Sodertalje (SE)

( * ) Notice: Subject to any disclaimer, the term of this patent is extended or adjusted under 35 U.S.C. 154(b) by 1015 days.

This patent is subject to a terminal disclaimer.

(21) Appl. No.: 11/547,048

(22) PCT Filed: Mar. 30, 2005

(86) PCT No.: PCT/GB2005/001153

§ 371 (c)(1),
(2), (4) Date: Oct. 2, 2006

(87) PCT Pub. No.: WO2005/095354

PCT Pub. Date: Oct. 13, 2005

(65) Prior Publication Data

US 2007/0208059 A1    Sep. 6, 2007

(30) Foreign Application Priority Data

Apr. 3, 2004 (GB) ................... 0407671.7
Sep. 18, 2004 (GB) ................... 0420781.7

(51) Int. Cl.
*A61K 31/454* (2006.01)
*C07D 211/18* (2006.01)

(52) U.S. Cl. ...................... 514/317; 546/192

(58) Field of Classification Search ................ 546/192; 514/317
See application file for complete search history.

(56) References Cited

U.S. PATENT DOCUMENTS 5,624,941 A    4/1997    Barth et al.

FOREIGN PATENT DOCUMENTS

| DE | 140 966 | 4/1980 |
|---|---|---|
| WO | WO 99/62871 | 12/1999 |
| WO | WO 99/62872 | 12/1999 |
| WO | WO 01/70700 | 9/2001 |
| WO | WO 03/007887 | 1/2003 |
| WO | WO 03/027076 | 4/2003 |
| WO | WO 03/040107 | 5/2003 |
| WO | WO 03/063781 | 8/2003 |
| WO | WO 03/075660 | 9/2003 |
| WO | WO 03/075921 | 9/2003 |
| WO | WO-2004/050367 | * 6/2004 |
| WO | WO 2004/060367 | 7/2004 |
| WO | WO 2004/060870 | 7/2004 |
| WO | WO 2004/099130 | 11/2004 |

OTHER PUBLICATIONS

U.S. Appl. No. 11/793,375, filed 2005, commonly assigned.*
U.S. Appl. No. 12/066,946, filed 2006, commonly assigned.*
U.S. Appl. No. 12/066,949, filed 2006, commonly assigned.*
Palmer et al. "Cannabinergic ligands" Chemistry and Physics of Lipids 121:3-19 (2002).
J.H.M. Lange, et al., "Bioisosteric Replacements of the Pyrazole Moiety of Rimonabant: Synthesis, Biological Properties, and Molecular Modeling Investigations of Thiazoles, Triazoles, and Imidazoles as Potent and Selective CB1 Cannabinoid Receptor Antagonists" Journal of Medicinal Chemistry 48: 1823-1838 (2005).

* cited by examiner

*Primary Examiner*—Joseph K. McKane
*Assistant Examiner*—Janet L Coppins
(74) *Attorney, Agent, or Firm*—Morgan Lewis & Bockius LLP

(57) ABSTRACT

The present invention relates to compounds of formula (I) and processes for preparing such compounds, their use in the treatment of obesity, psychiatric and neurological disorders, to methods for their therapeutic use and to pharmaceutical compositions containing them.

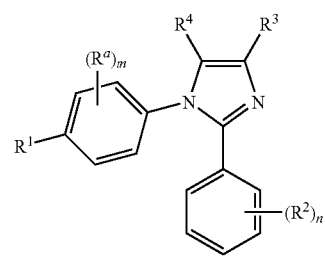

10 Claims, No Drawings

THERAPEUTIC AGENTS

CROSS-REFERENCE TO RELATED APPLICATIONS

This application is a national stage of PCT/GB2005/001153, filed Mar. 30, 2005, which claims priority to United Kingdom Application 0407671.7 filed Apr. 3, 2004, and UK 0420781.7 filed Sep. 18, 2004.

FIELD OF INVENTION

The present invention relates to certain 1,2-diarylimidazole-4-carboxamide compounds of formula I, to processes for preparing such compounds, to their use in the treatment of obesity, psychiatric and neurological disorders, to methods for their therapeutic use and to pharmaceutical compositions containing them.

BACKGROUND OF THE INVENTION

It is known that certain $CB_1$ modulators (known as antagonists or inverse agonists) are useful in the treatment of obesity, psychiatric and neurological disorders (WO01/70700 and EP 656354).

WO04/60367 and WO2004/099130 disclose that certain diaryl imidazoles and triazoles are useful as COX-1 inhibitors useful in the treatment of inflammation. Compounds exemplified in these applications are disclaimed from the claims of the present invention.

DD 140966 discloses that certain imidazolecarboxylic acid anilides are useful as plant growth regulators. Compounds exemplified in this application are disclaimed from the claims of the present invention.

WO 03/007887 and WO03/075660 disclose certain 4,5-diarylimidazole-2-carboxamides as $CB_1$ modulators.

WO03/27076 and WO 03/63781 disclose certain 1,2-diarylimidazole-4-carboxamides which are $CB_1$ modulators. Compounds exemplified in these applications are disclaimed from the claims of the present invention.

WO03/40107 discloses certain 1,2-diarylimidazole-4-carboxamides as being useful in the treatment of obesity and obesity-related disorders.

However, there is a need for $CB_1$ modulators with improved physicochemical properties and/or DMPK properties and/or pharmacodynamic properties.

DESCRIPTION OF THE INVENTION

The invention relates to a compound of formula (I)

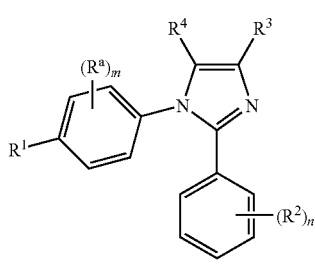

I and pharmaceutically acceptable salts thereof, in which
$R^1$ represents a) a $C_{1-6}$alkyl group optionally substituted by one or more fluoro b) a group of formula phenyl $(CH_2)_pO$— in which p is 1, 2 or 3 and the phenyl ring is optionally substituted by 1, 2 or 3 groups represented by Z, c) a group $R^5S(O)_2O$ or $R^5S(O)_2NH$ in which $R^5$ represents a $C_{1-10}$alkyl group optionally substituted by one or more fluoro, or $R^5$ represents phenyl or a heteroaryl group each of which is optionally substituted by 1, 2 or 3 groups represented by Z or d) a group of formula $(R^6)_3Si$ in which $R^6$ represents a $C_{1-6}$alkyl group which may be the same or different;

$R^a$ represents halo, a $C_{1-3}$alkyl group or a $C_{1-3}$alkoxy group;

m is 0, 1, 2 or 3;

$R^2$ represents a $C_{1-3}$alkyl group, a $C_{1-3}$alkoxy group, hydroxy, nitro, cyano or halo n is 0, 1, 2 or 3;

$R^3$ represents
a) a group X—Y—$NR^7R^8$
in which X is CO or $SO_2$,
Y is absent or represents NH optionally substituted by a $C_{1-3}$alkyl group;
and $R^7$ and $R^8$ independently represent:
a $C_{1-6}$alkyl group optionally substituted by 1, 2, or 3 groups represented by W;
a $C_{3-15}$cycloalkyl group optionally substituted by 1, 2, or 3 groups represented by W;
an optionally substituted ($C_{3-15}$cycloalkyl)$C_{1-3}$alkylene group optionally substituted by 1, 2, or 3 groups represented by W;
a group —$(CH_2)_r$(phenyl)$_s$ in which r is 0, 1, 2, 3 or 4, s is 1 when r is 0 otherwise s is 1 or 2 and the phenyl groups are optionally independently substituted by one, two or three groups represented by Z;
a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl;
a group —$(CH_2)_t$Het in which t is 0, 1, 2, 3 or 4, and the alkylene chain is optionally substituted by one or more $C_{1-3}$alkyl groups and Het represents a heteroaryl group optionally substituted by one, two or three groups selected from a $C_{1-5}$alkyl group, a $C_{1-5}$alkoxy group or halo wherein the alkyl and alkoxy group are optionally independently substituted by one of more fluoro;
or $R^7$ represents H and $R^8$ is as defined above;
or $R^7$ and $R^8$ together with the nitrogen atom to which they are attached represent a saturated or partially unsaturated 5 to 8 membered heterocyclic group containing one nitrogen and optionally one of the following: oxygen, sulphur or an additional nitrogen; wherein the heterocyclic group is optionally substituted by one or more $C_{1-3}$alkyl groups, hydroxy, fluoro or benzyl;
or b) oxazolyl, isoxazolyl, thiazolyl, isothiazolyl, oxadiazolyl, thiadiazolyl, pyrrolyl, pyrazolyl, imidazolyl, triazolyl, tetrazolyl, thienyl, furyl or oxazolinyl,
each optionally substituted by 1, 2 or 3 groups Z;
$R^4$ represents H, a $C_{1-6}$alkyl group, a $C_{1-6}$alkoxy group or a $C_{1-6}$alkoxy$C_{1-6}$alkylene group which contains a maximum of 6 carbon atoms, each of which groups is optionally substituted by one or more fluoro or cyano;
Z represents a $C_{1-3}$alkyl group, a $C_{1-3}$alkoxy group, hydroxy, halo, trifluoromethyl, trifluoromethylthio, difluoromethoxy, trifluoromethoxy, trifluoromethylsulphonyl, nitro, amino, mono or di $C_{1-3}$alkylamino, $C_{1-3}$alkylsulphonyl, $C_{1-3}$alkoxycarbonyl, carboxy, cyano, carbamoyl, mono or di $C_{1-3}$alkyl carbamoyl and acetyl; and
W represents hydroxy, fluoro, a $C_{1-3}$alkyl group, a $C_{1-3}$alkoxy group, amino, mono or di $C_{1-3}$alkylamino, or a heterocyclic amine selected from morpholinyl, pyrrolidinyl, piperidinyl or piperazinyl in which the heterocyclic amine is optionally substituted by a $C_{1-3}$alkyl group or hydroxyl;

with the proviso that when n is 1 then $R^2$ is not methoxy in either the 2-position or the 4-position of the phenyl ring and the further proviso that $R^1$ is not methylsulfonylamino, methoxy or $CF_3O$—.

In a particular group of compounds of formula (I)

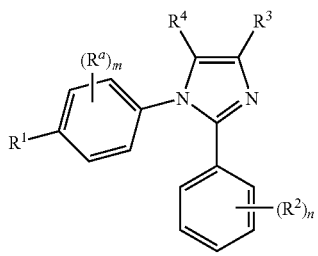

I and pharmaceutically acceptable salts thereof, in which $R^1$ represents a) a $C_{1-6}$alkoxy group optionally substituted by one or more fluoro b) a group of formula phenyl $(CH_2)_pO$— in which p is 1, 2 or 3 and the phenyl ring is optionally substituted by 1, 2 or 3 groups represented by Z, c) a group $R^5S(O)_2O$ or $R^5S(O)_2NH$ in which $R^5$ represents a $C_{1-6}$alkyl group optionally substituted by one or more fluoro, or $R^5$ represents phenyl or a heteroaryl group each of which is optionally substituted by 1, 2 or 3 groups represented by Z or d) a group of formula $(R^6)_3Si$ in which $R^6$ represents a $C_{1-6}$alkyl group which may be the same or different;

$R^a$ represents halo, a $C_{1-3}$alkyl group or a $C_{1-3}$alkoxy group;

m is 0, 1, 2 or 3;

$R^2$ represents a $C_{1-3}$alkyl group, a $C_{1-3}$alkoxy group, hydroxy, nitro, cyano or halo n is 0, 1, 2 or 3;

$R^3$ represents a) a group X—Y—$NR^7R^8$ in which X is CO or $SO_2$,

Y is absent or represents NH optionally substituted by a $C_{1-3}$alkyl group;

and $R^7$ and $R^8$ independently represent:

a $C_{1-6}$alkyl group optionally substituted by 1, 2, or 3 groups represented by W;

a $C_{3-15}$cycloalkyl group optionally substituted by 1, 2, or 3 groups represented by W;

an optionally substituted $(C_{3-15}$cycloalkyl$)C_{1-3}$alkylene group optionally substituted by 1, 2, or 3 groups represented by W;

a group —$(CH_2)_r$(phenyl)$_s$ in which r is 0, 1, 2, 3 or 4, s is 1 when r is 0 otherwise s is 1 or 2 and the phenyl groups are optionally independently substituted by one, two or three groups represented by Z;

a saturated 5 to 8 membered heterocyclic group containing one nitrogen and optionally one of the following: oxygen, sulphur or an additional nitrogen wherein the heterocyclic group is optionally substituted by one or more $C_{1-3}$alkyl groups, hydroxy or benzyl;

a group —$(CH_2)_t$ Het in which t is 0, 1, 2, 3 or 4, and the alkylene chain is optionally substituted by one or more $C_{1-3}$alkyl groups and Het represents a heteroaryl group optionally substituted by one, two or three groups selected from a $C_{1-5}$alkyl group, a $C_{1-5}$alkoxy group or halo;

or $R^7$ represents H and $R^8$ is as defined above;

or $R^7$ and $R^8$ together with the nitrogen atom to which they are attached represent a saturated or partially unsaturated 5 to 8 membered heterocyclic group containing one nitrogen and optionally one of the following: oxygen, sulphur or an additional nitrogen; wherein the heterocyclic group is optionally substituted by one or more $C_{1-3}$alkyl groups, hydroxy, fluoro or benzyl;

or b) oxazolyl, isoxazolyl, thiazolyl, isothiazolyl, oxadiazolyl, thiadiazolyl, pyrrolyl, pyrazolyl, imidazolyl, triazolyl, tetrazolyl, thienyl, furyl or oxazolinyl, each optionally substituted by 1, 2 or 3 groups Z;

$R^4$ represents H, a $C_{1-6}$alkyl group, a $C_{1-6}$alkoxy group or a $C_{1-6}$alkoxy$C_{1-6}$alkylene group which contains a maximum of 6 carbon atoms, each of which groups is optionally substituted by one or more fluoro or cyano;

Z represents a $C_{1-3}$alkyl group, a $C_{1-3}$alkoxy group, hydroxy, halo, trifluoromethyl, trifluoromethylthio, difluoromethoxy, trifluoromethoxy, trifluoromethylsulphonyl, nitro, amino, mono or di $C_{1-3}$alkylamino, $C_{1-3}$alkylsulphonyl, $C_{1-3}$alkoxycarbonyl, carboxy, cyano, carbamoyl, mono or di $C_{1-3}$alkyl carbamoyl and acetyl; and W represents hydroxy, fluoro, a $C_{1-3}$alkyl group, a $C_{1-3}$alkoxy group, amino, mono or di $C_{1-3}$alkylamino, or a heterocyclic amine selected from morpholinyl, pyrrolidinyl, piperidinyl or piperazinyl in which the heterocyclic amine is optionally substituted by a $C_{1-3}$alkyl group or hydroxyl;

with the proviso that when n is 1 then $R^2$ is not methoxy in either the 2-position or the 4-position of the phenyl ring and the further proviso that $R^1$ is not methylsulfonylamino, methoxy or $CF_3O$—.

In a particular group of compounds of formula (I)

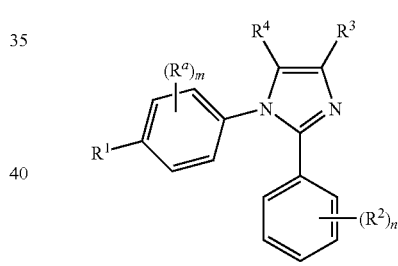

I and pharmaceutically acceptable salts thereof, $R^1$ represents a) a $C_{3-6}$alkoxy group substituted by one or more fluoro or b) a group of formula phenyl$(CH_2)_pO$— in which p is 1, 2 or 3 and the phenyl ring is optionally substituted by 1, 2 or 3 groups represented by Z, or c) a group $R^5S(O)_2O$ in which $R^5$ represents a $C_{1-6}$alkyl group optionally substituted by one or more fluoro, or $R^5$ represents phenyl or a heteroaryl group each of which is optionally substituted by 1, 2 or 3 groups represented by Z;

$R^a$ represents halo, a $C_{1-3}$alkyl group or a $C_{1-3}$alkoxy group;

m is 0, 1, 2 or 3;

$R^2$ represents halo n is 0, 1, 2 or 3;

$R^3$ represents a) a group X—Y—$NR^7R^8$ in which X is CO;

Y is absent or represents NH optionally substituted by a $C_{1-3}$alkyl group;

and $R^7$ and $R^8$ independently represent:

a $C_{1-6}$alkyl group optionally substituted by 1, 2, or 3 groups represented by W;

a C$_{3-15}$cycloalkyl group optionally substituted by 1, 2, or 3 groups represented by W;

an optionally substituted (C$_{3-15}$cycloalkyl)C$_{1-3}$alkylene group optionally substituted by 1, 2, or 3 groups represented by W;

a group —(CH$_2$)$_r$(phenyl)$_s$ in which r is 0, 1, 2, 3 or 4, s is 1 when r is 0 otherwise s is 1 or 2 and the phenyl groups are optionally independently substituted by one, two or three groups represented by Z;

a saturated 5 to 8 membered heterocyclic group containing one nitrogen and optionally one of the following: oxygen, sulphur or an additional nitrogen wherein the heterocyclic group is optionally substituted by one or more C$_{1-3}$alkyl groups, hydroxy or benzyl;

a group —(CH$_2$)$_t$ Het in which t is 0, 1, 2, 3 or 4, and the alkylene chain is optionally substituted by one or more C$_{1-3}$alkyl groups and Het represents a heteroaryl group optionally substituted by one, two or three groups selected from a C$_{1-5}$alkyl group, a C$_{1-5}$alkoxy group or halo;

or R$^7$ represents H and R$^8$ is as defined above;

or R$^7$ and R$^8$ together with the nitrogen atom to which they are attached represent a saturated or partially unsaturated 5 to 8 membered heterocyclic group containing one nitrogen and optionally one of the following: oxygen, sulphur or an additional nitrogen; wherein the heterocyclic group is optionally substituted by one or more C$_{1-3}$alkyl groups, hydroxy, fluoro or benzyl;

R$^4$ represents H, a C$_{1-6}$alkyl group, a C$_{1-6}$alkoxy group or a C$_{1-6}$alkoxyC$_{1-6}$alkylene group which contains a maximum of 6 carbon atoms, each of which groups is optionally substituted by one or more fluoro or cyano;

Z represents a C$_{1-3}$alkyl group, a C$_{1-3}$alkoxy group, hydroxy, halo, trifluoromethyl, trifluoromethylthio, difluoromethoxy, trifluoromethoxy, trifluoromethylsulphonyl, nitro, amino, mono or di C$_{1-3}$alkylamino, C$_{1-3}$alkylsulphonyl, C$_{1-3}$alkoxycarbonyl, carboxy, cyano, carbamoyl, mono or di C$_{1-3}$alkyl carbamoyl and acetyl; and W represents hydroxy; fluoro, a C$_{1-3}$alkyl group, a C$_{1-3}$alkoxy group, amino, mono or di C$_{1-3}$alkylamino, or a heterocyclic amine selected from morpholinyl, pyrrolidinyl, piperidinyl or piperazinyl in which the heterocyclic amine is optionally substituted by a C$_{1-3}$alkyl group or hydroxyl.

In a particular group of compounds of formula I, R$^1$ represents a group R$^5$S(O)$_2$O in which R$^5$ represents a C$_{1-6}$alkyl group, particularly a C$_{2-6}$alkyl group, each optionally substituted by one or more fluoro and in which R$^2$, R$^3$, R$^4$, R$^a$, m and n are as previously defined.

In a particular group of compounds of formula I, R$^3$ represents a group CONHNR$^7$R$^8$ in which NR$^7$R$^8$ represents piperidino and R$^1$, R$^2$, R$^4$, R$^a$, m and n are as previously defined.

It will be understood that where a substituent Z is present in more than one group or where more than one substituent Z is present in the same group that these substituents are independently selected and may be the same or different. The same is true for W. Similarly when m is 2 or 3 then the groups R$^a$ are independently selected so that they may be the same or different and similarly when n is 2 or 3 then the groups R$^2$ are independently selected so that they may be the same or different. Similarly when R$^5$ and R$^7$ and/or R$^8$ contain a heteroaryl group the heteroaryl groups and their optional substituents are independently selected so that they may be the same or different.

The term C$_{3-15}$cycloalkyl includes monocyclic, bicyclic, tricyclic and spiro systems for example, cyclopentyl, cyclohexyl and adamantyl.

The term heteroaryl means an aromatic 5-, 6-, or 7-membered monocyclic ring or a 9- or 10-membered bicyclic ring, with up to five ring heteroatoms selected from oxygen, nitrogen and sulfur. Suitable aromatic heteroaryl groups include, for example furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazinyl, benzofuranyl, indolyl, benzothienyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl. Preferably furyl, pyrrolyl, thienyl, oxazolyl, isoxazolyl, imidazolyl, pyrazolyl, oxazolyl thiazolyl, isothiazolyl, oxadiazolyl, thiadiazolyl, triazolyl, tetrazolyl, pyridyl, pyridazinyl, pyrimidinyl, pyrazinyl or 1,3,5-triazenyl and more preferably pyrrolyl, thienyl, imidazolyl, oxazolyl or pyridyl.

Suitable saturated or partially unsaturated 5 to 8 membered heterocyclic groups containing one or more heteroatoms selected from nitrogen, oxygen or sulphur include, for example tetrahydrofuranyl, tetrahydropyranyl, 2,3-dihydro-1,3-thiazolyl, 1,3-thiazolidinyl, pyrrolinyl, pyrrolidinyl, morpholinyl, tetrahydro-1,4-thiazinyl, 1-oxotetrahydrothienyl, 1,1-dioxotetrahydro-1,4-thiazinyl, piperidinyl, homopiperidinyl, piperazinyl, homopiperazinyl, dihydropyridinyl, tetrahydropyridinyl, dihydropyrimidinyl or tetrahydropyrimidinyl, preferably tetrahydrofuranyl, tetrahydropyranyl, pyrrolidinyl, morpholinyl, piperidinyl or piperazinyl, more preferably tetrahydrofuran-3-yl, tetrahydropyran-4-yl, pyrrolidin-3-yl, morpholino, piperidino, piperidin-4-yl or piperazin-1-yl.

Suitable groups in which R$^1$ represents a group R$^5$S(O)$_2$O in which R$^5$ represents a C$_{1-6}$alkyl group optionally substituted by one or more fluoro include methanesulfonyloxy, ethanesulfonyloxy, n-propylsulfonyloxy, n-butylsulfonyloxy, 3-methylbutane-1-sulfonyloxy, 3,3-dimethylbutane-1-sulfonyloxy, fluoromethylsulfonyloxy, difluoromethylsulfonyloxy, trifluoromethylsulfonyloxy, mono, di or tri (fluoroethyl)sulfonyloxy, 3,3,3-trifluoropropyl-1-sulfonyloxy, or 4,4,4-trifluorobutyl-1-sulfonyloxy, Suitable groups in which R$^1$ represents a C$_{1-6}$alkoxy group optionally substituted by one or more fluoro include butoxy, pentyloxy, hexyloxy, fluoromethoxy, difluoromethoxy, trifluoroethoxy, 4,4,4-trifluorobutoxy, 5,5,5,-trifluoropentyloxy and 6,6,6-trifluorohexyloxy.

Suitable groups in which R$^1$ represents a group R$^5$S(O)$_2$O in which R$^5$ represents phenyl or a heteroaryl group each of which is optionally substituted by 1, 2 or 3 groups represented by Z include phenylsulfonyloxy, thienylsulfonyloxy or pyridylsulfonyloxy optionally substituted by 1, 2 or 3 groups represented by Z.

A particular group of compounds of formula I is represented by formula IA

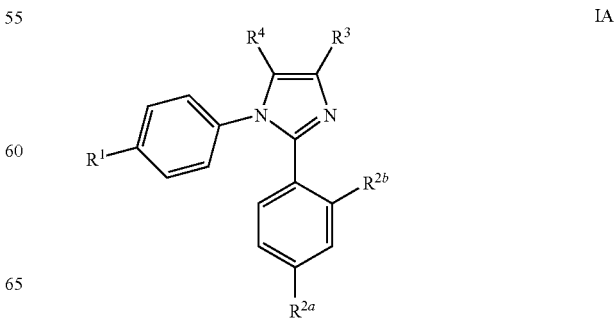

IA in which $R^1$ is a) a $C_{3-6}$alkoxy group substituted by one or more fluoro, b) a group of formula phenyl$(CH_2)_pO$— in which p is 1, 2 or 3 and the phenyl ring is optionally substituted by 1, 2 or 3 groups represented by Z, c) a group $R^5S(O)_2O$ in which $R^5$ represents a $C_{1-10}$alkyl group optionally substituted by one or more fluoro or $R^5$ represents thienyl or pyridyl each of which is optionally substituted by one or more halo;

$R^{2a}$ represents H or chloro;

$R^{2b}$ represents H or chloro;

$R^3$ represents a group $CONHNR^7R^8$ in which $NR^7R^8$ represents piperidino or $R^3$ represents a group $CONR^7R^8$ in which $R^7$ is H and $R^8$ is pyridyl optionally substituted by halo or trifluoromethyl; and $R^4$ represents a $C_{1-3}$alkyl group.

Further values of $R^{2a}$, $R^{2b}$, $R^4$, $R^5$, $R^7$, and $R^8$ in compounds of formula I and of formula IA now follow. It will be understood that such values may be used where appropriate with any of the definitions, claims or embodiments defined hereinbefore or hereinafter.

Particularly in compounds of formula IA described immediately above $R^1$ represents a group $R^5S(O)_2O$ in which $R^5$ represents a $C_{2-7}$alkyl group optionally substituted by one or more fluoro. Particularly in compounds of formula IA described immediately above $R^1$ represents a group $R^5S(O)_2O$ in which $R^5$ represents 2-thienyl optionally substituted by chloro or $R^5$ represents 3-pyridyl. Particularly in compounds of formula IA described immediately above $R^{2a}$ represents chloro and $R^{2b}$ represents chloro. Particularly in compounds of formula IA described immediately above $R^3$ represents a group $CONHNR^7R^8$ in which $NR^7R^8$ represents piperidino. Particularly in compounds of formula IA described immediately above $R^3$ represents a group $CONR^7R^8$ in which $R^7$ is H and $R^8$ is pyridyl optionally substituted by trifluoromethyl. Particularly in compounds of formula IA described immediately above $R^4$ is methyl.

A further particular group of compounds of formula I is represented by formula IA

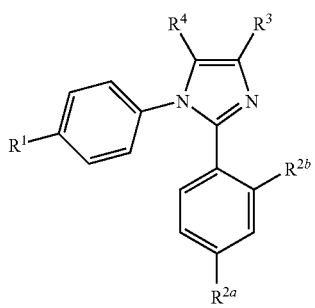

IA in which $R^1$ is a) a $C_{3-6}$alkoxy group substituted by one or more fluoro, b) a group of formula phenyl$(CH_2)_pO$— in which p is 1, 2 or 3 and the phenyl ring is optionally substituted by 1, 2 or 3 groups represented by Z, c) a group $R^5S(O)_2O$ in which $R^5$ represents a $C_{1-6}$alkyl group optionally substituted by one or more fluoro;

$R^{2a}$ represents H or chloro;

$R^{2b}$ represents H or chloro;

$R^3$ represents a group $CONHNR^7R^8$ in which $NR^7R^8$ represents piperidino; and $R^4$ represents a $C_{1-3}$alkyl group.

Further values of $R^1$ in compounds of formula I and of formula IA now follow. It will be understood that such values may be used where appropriate with any of the definitions, claims or embodiments defined hereinbefore or hereinafter.

In one group of compounds of formula I or formula IA, $R^1$ is a $C_{3-6}$alkoxy group substituted by one or more fluoro. In a second group of compounds of formula I or formula IA, $R^1$ is a $C_{4-6}$alkoxy group optionally substituted by one or more fluoro. In a third group of compounds of formula I or formula IA, $R^1$ is a $C_{4-6}$alkoxy group substituted by one or more fluoro. In a fourth group of compounds of formula I or formula IA, $R^1$ is a group of formula phenyl$(CH_2)_pO$— in which p is 1, 2 or 3. In a fifth group of compounds of formula I or formula IA, $R^1$ is a group $R^5S(O)_2O$ in which $R^5$ represents a $C_{1-6}$alkyl group optionally substituted by one or more fluoro.

Particularly $R^1$ is 4,4,4-trifluorobutoxy, n-butylsulfonyloxy, n-propylsulfonyloxy, n-ethylsulfonyloxy, benzyloxy, 4,4,4-trifluorobutyl-1-sulfonyloxy or 3,3,3-trifluoropropyl-1-sulfonyloxy. More particularly $R^1$ is 4,4,4-trifluorobutoxy, n-butylsulfonyloxy, n-propylsulfonyloxy, ethylsulfonyloxy or benzyloxy.

Another particular group of compounds of formula I is represented by formula IA

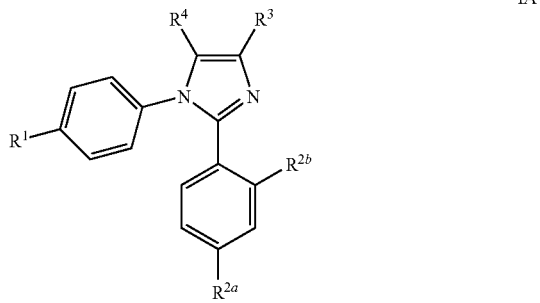

IA in which $R^1$ is a) a $C_{3-6}$alkoxy group substituted by one or more fluoro or b) a group $R^5S(O)_2O$ in which $R^5$ represents a $C_{1-6}$alkyl group optionally substituted by one or more fluoro, or $R^5$ represents phenyl or a heteroaryl group each of which is optionally substituted by 1, 2 or 3 groups represented by Z;

$R^{2a}$ represents chloro;

$R^{2b}$ represents chloro;

$R^3$ represents a group $CONHNR^7R^8$ in which $NR^7R^8$ represents piperidino; and $R^4$ represents a $C_{1-3}$alkyl group.

In a particular group of compounds of formula IA, $R^1$ represents a group $R^5S(O)_2O$ in which $R^5$ represents a $C_{1-6}$alkyl group optionally substituted by one or more fluoro;

$R^{2a}$ represents chloro;

$R^{2b}$ represents chloro;

$R^3$ represents a group $CONHNR^7R^8$ in which $NR^7R^8$ represents piperidino; and $R^4$ represents a $C_{1-3}$alkyl group.

In a particular group of compounds of formula IA, $R^1$ represents a $C_{4-6}$alkoxy group optionally substituted by one or more fluoro;

$R^{2a}$ represents chloro;

$R^{2b}$ represents chloro;

$R^3$ represents a group $CONHNR^7R^8$ in which $NR^7R^8$ represents piperidino; and $R^4$ represents a $C_{1-3}$alkyl group.

In a particular group of compounds of formula IA, $R^1$ represents a $C_{4-6}$alkoxy group substituted by one or more fluoro;

$R^{2a}$ represents chloro;

$R^{2b}$ represents chloro;

$R^3$ represents a group $CONHNR^7R^8$ in which $NR^7R^8$ represents piperidino; and $R^4$ represents a $C_{1-3}$alkyl group.

"Pharmaceutically acceptable salt", where such salts are possible, includes both pharmaceutically acceptable acid and base addition salts. A suitable pharmaceutically acceptable salt of a compound of Formula I is, for example, an acid-addition salt of a compound of Formula I which is sufficiently basic, for example an acid-addition salt with an inorganic or organic acid such as hydrochloric, hydrobromic, sulphuric, trifluoroacetic, citric or maleic acid; or, for example a salt of a compound of Formula I which is sufficiently acidic, for example an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine.

Throughout the specification and the appended claims, a given chemical formula or name shall encompass all stereo and optical isomers and racemates thereof as well as mixtures in different proportions of the separate enantiomers, where such isomers and enantiomers exist, as well as pharmaceutically acceptable salts thereof and solvates thereof such as for instance hydrates. Isomers may be separated using conventional techniques, e.g. chromatography or fractional crystallization. The enantiomers may be isolated by separation of racemate for example by fractional crystallization, resolution or HPLC. The diastereomers may be isolated by separation of isomer mixtures for instance by fractional crystallization, HPLC or flash chromatography. Alternatively the stereoisomers may be made by chiral synthesis from chiral starting materials under conditions which will not cause racemisation or epimerisation, or by derivatisation, with a chiral reagent. All stereoisomers are included within the scope of the invention. All tautomers, where possible, are included within the scope of the invention. The present invention also encompasses compounds containing one or more isotopes for example $^{14}C$, $^{11}C$ or $^{19}F$ and their use as isotopically labelled compounds for pharmacological and metabolic studies.

The present invention also encompasses prodrugs of a compound of formula I that is compounds which are converted into a compound of formula I in vivo.

The following definitions shall apply throughout the specification and the appended claims.

Unless otherwise stated or indicated, the term "alkyl" denotes either a straight or branched alkyl group. Examples of said alkyl include methyl, ethyl, n-propyl, isopropyl, n-butyl, iso-butyl, sec-butyl and t-butyl. Preferred alkyl groups are methyl, ethyl, propyl, isopropyl and tertiary butyl.

Unless otherwise stated or indicated, the term "alkoxy" denotes a group O-alkyl, wherein alkyl is as defined above.

Unless otherwise stated or indicated, the term "halogen" shall mean fluorine, chlorine, bromine or iodine.

Specific compounds of the invention are one or more of the following:

1-(4-benzyloxy-phenyl)-2-(2,4-dichlorophenyl)-5-methyl-1H-imidazole-4-carboxylic acid piperidin-1-ylamide;

ethanesulfonic acid 4-[2-(2,4-dichlorophenyl)-5-methyl-4-(piperidin-1-ylcarbamoyl)-imidazol-1-yl]phenyl ester;

propane-1-sulfonic acid 4-[2-(2,4-dichlorophenyl)-5-methyl-4-(piperidin-1-ylcarbamoyl)-imidazol-1-yl]-phenyl ester;

butane-1-sulfonic acid 4-[2-(2,4-dichlorophenyl)-5-methyl-4-(piperidin-1-ylcarbamoyl)-imidazol-1-yl]-phenyl ester;

2-(2,4-dichloro-phenyl)-5-methyl-1-[4-(4,4,4-trifluorobutoxy)phenyl]-1H-imidazole-4-carboxylic acid piperidin-1-ylamide;

3,3,3-trifluoropropane-1-sulfonic acid 4-[2-(2,4-dichlorophenyl)-5-methyl-4-(piperidin-1-ylcarbamoyl)imidazol-1-yl]phenyl ester;

4,4,4-trifluorobutane-1-sulfonic acid 4-[2-(2,4-dichlorophenyl)-5-methyl-4-(piperidin-1-ylcarbamoyl)imidazol-1-yl] phenyl ester;

4-{2-(2,4-dichlorophenyl)-5-methyl-4-[(piperidin-1-ylamino)carbonyl]-1H-imidazol-1-yl}phenyl thiophene-2-sulfonate;

4-{2-(2,4-dichlorophenyl)-5-methyl-4-[(piperidin-1-ylamino)carbonyl]-1H-imidazol-1-yl}phenyl pyridine-3-sulfonate;

4-{2-(2,4-dichlorophenyl)-5-methyl-4-[(piperidin-1-ylamino)carbonyl]-1H-imidazol-1-yl}phenyl pyridine-3-sulfonate;

4-{2-(2,4-dichlorophenyl)-5-methyl-4-[(piperidin-1-ylamino)carbonyl]-1H-imidazol-1-yl}phenyl 3-methylbutane-1-sulfonate;

4-{2-(2,4-dichlorophenyl)-5-methyl-4-[(piperidin-1-ylamino)carbonyl]-1H-imidazol-1-yl}phenyl 3,3-dimethylbutane-1-sulfonate;

4-[2-(2,4-dichlorophenyl)-5-methyl-4-({[5-(trifluoromethyl)pyridin-2-yl]amino}carbonyl)-1H-imidazol-1-yl] phenyl 3,3,3-trifluoropropane-1-sulfonate;

4-[2-(2,4-dichlorophenyl)-5-methyl-4-({[5-(trifluoromethyl)pyridin-2-yl]amino}carbonyl)-1H-imidazol-1-yl] phenyl 3-methylbutane-1-sulfonate;

and pharmaceutically acceptable salts thereof.

Methods of Preparation

The compounds of the invention may be prepared as outlined below according to any of the following methods. However, the invention is not limited to these methods, the compounds may also be prepared as described for structurally related compounds in the prior art.

Compounds of formula I in which $R^1$ represents a) a $C_{3-6}$alkoxy group substituted by one or more fluoro or b) a group of formula phenyl$(CH_2)_pO$— in which p is 1, 2 or 3 and the phenyl ring is optionally substituted by 1, 2 or 3 groups represented by Z, or c) a group $R^5S(O)_2O$ may be prepared by reacting a compound of formula II

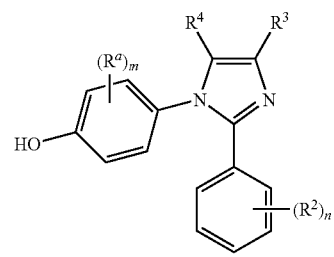

in which $R^2$, $R^3$, $R^4$, $R^a$, m and n are as previously defined with a group $R^{14}$—X in which $R^{14}$ represents a group such that $R^{14}O$ represents $R^1$ and X represents a leaving group for example halo, at a temperature in the range of −25 to 150° C., in the presence of an inert solvent, for example dichloromethane, and optionally in the presence of a base for example triethylamine or pyridine.

Compounds of formula I in which $R^a$, $R^1$, $R^2$, $R^4$, m and n are as previously defined and $R^3$ represents a group X—Y—$NR^7R^8$ in which X is CO and Y, $R^7$ and $R^8$ are as previously defined may be prepared by reacting a compound of formula III

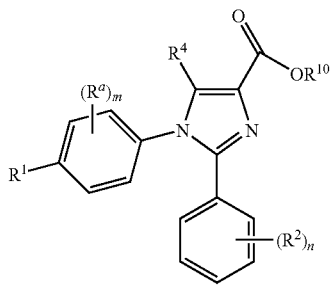

in which $R^a$, $R^1$, $R^2$, $R^4$, m and n are as previously defined and $R^{10}$ represents H or a $C_{1-6}$alkyl group with a compound of formula IV or a salt thereof

$R^7R^8YNH_2$      IV in which Y, $R^7$ and $R^8$ are as previously defined, in an inert solvent, for example toluene, in the presence of a Lewis Acid, for example trimethylaluminium, at a temperature in the range of −25° C. to 150° C. when $R^{10}$ is a $C_{1-6}$alkyl group; or alternatively when $R^{10}$ is H by reacting a compound of formula III with a chlorinating agent for example oxalyl chloride, and then reacting the acid chloride produced with an amine of formula IV in an inert solvent, for example dichloromethane, in the presence of a base, for example triethylamine, at a temperature in the range of −25° C. to 150° C.

Compounds of formula I in which $R^a$, $R^1$, $R^2$, $R^4$, m and n are as previously defined and $R^3$ represents a group X—Y—$NR^7R^8$ in which X is $SO_2$ may be prepared by reacting a compound of formula V

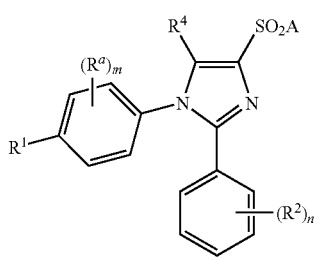

in which $R^a$, $R^1$, $R^2$, $R^4$, m and n are as previously defined and A represents a leaving group, for example halo eg chloro, with a compound of formula IV in which Y, $R^7$ and $R^8$ are as previously defined or a salt thereof in an inert solvent, for example THF or dichloromethane, in the presence of a base, for example potassium carbonate, triethylamine or pyridine, at a temperature in the range of −25° C. to 150° C.

Compounds of formula I in which $R^a$, $R^2$, $R^3$, $R^4$, m and n are as previously defined and $R^1$ represents a group $R^5S(O)_2$NH may be prepared by reacting a compound of formula VI

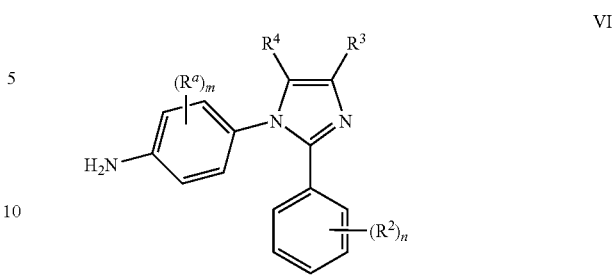

in which $R^a$, $R^2$, $R^3$, $R^4$, m and n are as previously defined with a sulphonating agent of formula $R^5SO_2L$ in which $R^5$ is as previously defined and L represents a leaving group, for example chloro, in an inert solvent, for example dichloromethane, in the presence of a base, for example triethylamine, at a temperature in the range of −25° C. to 150° C. Certain intermediate compounds are believed to be novel and form part of the present invention, particularly compounds of formula III as defined above and including each and every definition of $R^1$ given previously.

Compounds of formula II, III, V and VI may be prepared by the general synthetic route shown at the end of the examples and adaptations thereof or by analogous methods known to those skilled in the art. It will be appreciated by those skilled in the art that during the reaction sequence certain functional groups will require protection followed by deprotection at an appropriate stage see "Protective Groups in Organic Synthesis", 3rd Edition (1999) by Greene and Wuts.

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable addition salt, in a pharmaceutically acceptable dosage form. Depending upon the disorder and patient to be treated and the route of administration, the compositions may be administered at varying doses.

Suitable daily doses of the compounds of the invention in the therapeutic treatment of humans are about 0.001-10 mg/kg body weight, preferably 0.01-1 mg/kg body weight. Oral formulations are preferred particularly tablets or capsules which may be formulated by methods known to those skilled in the art to provide doses of the active compound in the range of 0.5 mg to 500 mg for example 1 mg, 3 mg, 5 mg, 10 mg, 25 mg, 50 mg, 100 mg and 250 mg.

According to a further aspect of the invention there is also provided a pharmaceutical formulation including any of the compounds of the invention, or pharmaceutically acceptable derivatives thereof, in admixture with pharmaceutically acceptable adjuvants, diluents and/or carriers.

Pharmacological Properties

The compounds of formula (I) are useful for the treatment of obesity or being overweight, is (e.g., promotion of weight loss and maintenance of weight loss), prevention of weight gain (e.g., medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items), for the treatment of psychiatric disorders such as psychotic and/or mood disorders, schizophrenia and schizo-affective disorder, bipolar disorders, anxiety, anxio-depressive disorders, depression, mania, obsessive-compulsive disorders, impulse control disorders (e.g., Gilles de la Tourette's syndrome), attention disorders like ADD/ADHD, stress, and neurological disorders such as dementia and cognitive and/or memory dysfunction (e.g., amnesia, Alzheimer's disease, Pick's dementia, dementia of ageing, vascular dementia, mild cognitive impairment, age-related cognitive decline, and mild dementia of ageing), neurological and/or neurodegenerative disorders (e.g. Multiple Sclerosis, Raynaud's syndrome, Parkinson's disease, Huntington's chorea and Alzheimer's disease), demyelinisation-related disorders, neuroinflammatory disorders (e.g., Guillain-Barré syndrome).

The compounds are also potentially useful for the prevention or treatment of dependence and addictive disorders and behaviours (e.g., alcohol and/or drug abuse, pathological gambling, kleptomania), drug withdrawal disorders (e.g., alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances), alcohol and/or drug-induced mood, anxiety and/or sleep disorder with onset during withdrawal, and alcohol and/or drug relapse.

The compounds are also potentially useful for the prevention or treatment of neurological dysfunctions such as dystonias, dyskinesias, akathisia, tremor and spasticity, treatment of spinal cord injury, neuropathy, migraine, vigilance disorders, sleep disorders (e.g., disturbed sleep architecture, sleep apnea, obstructive sleep apnea, sleep apnea syndrome), pain disorders, cranial trauma.

The compounds are also potentially useful for the treatment of immune, cardiovascular disorders (e.g. atherosclerosis, arteriosclerosis, angina pectoris, abnormal heart rhythms, and arrhythmias, congestive heart failure, coronary artery disease, heart disease, hypertension, prevention and treatment of left ventricular hypertrophy, myocardial infarction, transient ischaemic attack, peripheral vascular disease, systemic inflammation of the vasculature, septic chock, stroke, cerebral apoplexy, cerebral infarction, cerebral ischaemia, cerebral thrombosis, cerebral embolism, cerebral hemorrhagia, metabolic disorders (e.g. conditions showing reduced metabolic activity or a decrease in resting energy expenditure as a percentage of total fat-free mass, diabetes mellitus, dyslipidemia, fatty liver, gout, hypercholesterolemia, hyperlipidemia, hypertriglyceridemia, hyperuricacidemia, impaired glucose tolerance, impaired fasting glucose, insulin resistance, insulin resistance syndrome, metabolic syndrome, syndrome X, obesity-hypoventilation syndrome (Pickwickian syndrome), type I diabetes, type II diabetes, low HDL- and/or high LDL-cholesterol levels, low adiponectin levels), reproductive and endocrine disorders (e.g. treatment of hypogonadism in males, treatment of infertility or as contraceptive, menstrual abnormalities/emmeniopathy, polycystic ovarian disease, sexual and reproductive dysfunction in women and men (erectile dysfunction), GH-deficient subjects, hirsutism in females, normal variant short stature) and diseases related to the respiratory (e.g. asthma and chronic obstructive pulmonary disease) and gastrointestinal systems (e.g. dysfunction of gastrointestinal motility or intestinal propulsion, diarrhea, emesis, nausea, gallbladder disease, cholelithiasis, obesity-related gastro-esophageal reflux, ulcers).

The compounds are also potentially useful as agents in treatment of dermatological disorders, cancers (e.g. colon, rectum, prostate, breast, ovary, endometrium, cervix, gall-bladder, bile duct), craniopharyngioma, Prader-Willi syndrome, Turner syndrome, Frohlich's syndrome, glaucoma, infectious diseases, urinary tract disorders and inflammatory disorders (e.g. arthritis deformans, inflammation, inflammatory sequelae of viral encephalitis, osteoarthritis) and orthopedic disorders. The compounds are also potentially useful as agents in treatment of (esophageal) achalasia.

In another aspect the present invention provides a compound of formula I as previously defined for use as a medicament.

In a further aspect the present invention provides the use of a compound of formula I in the preparation of a medicament for the treatment or prophylaxis of obesity or being overweight, (e.g., promotion of weight loss and maintenance of weight loss), prevention of weight gain (e.g., medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items), for the treatment of psychiatric disorders such as psychotic and/or mood disorders, schizophrenia and schizo-affective disorder, bipolar disorders, anxiety, anxio-depressive disorders, depression, mania, obsessive-compulsive disorders, impulse control disorders (e.g., Gilles de la Tourette's syndrome), attention disorders like ADD/ADHD, stress, and neurological disorders such as dementia and cognitive and/or memory dysfunction (e.g., amnesia, Alzheimer's disease, Pick's dementia, dementia of ageing, vascular dementia, mild cognitive impairment, age-related cognitive decline, and mild dementia of ageing), neurological and/or neurodegenerative disorders (e.g. Multiple Sclerosis, Raynaud's syndrome, Parkinson's disease, Huntington's chorea and Alzheimer's disease), demyelinisation-related disorders, neuroinflammatory disorders (e.g., Guillain-Barré syndrome).

In a further aspect the present invention provides the use of a compound of formula I in the preparation of a medicament for the treatment or prophylaxis of dependence and addictive disorders and behaviours (e.g., alcohol and/or drug abuse, pathological gambling, kleptomania), drug withdrawal disorders (e.g., alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances), alcohol and/or drug-induced mood, anxiety and/or sleep disorder with onset during withdrawal, and alcohol and/or drug relapse.

In a further aspect the present invention provides the use of a compound of formula I in the preparation of a medicament for the treatment or prophylaxis of neurological dysfunctions such as dystonias, dyskinesias, akathisia, tremor and spasticity, treatment of spinal cord injury, neuropathy, migraine, vigilance disorders, sleep disorders (e.g., disturbed sleep architecture, sleep apnea, obstructive sleep apnea, sleep apnea syndrome), pain disorders, cranial trauma.

In a further aspect the present invention provides the use of a compound of formula I in the preparation of a medicament for the treatment or prophylaxis of immune, cardiovascular disorders (e.g. atherosclerosis, arteriosclerosis, angina pectoris, abnormal heart rhythms, and arrhythmias, congestive heart failure, coronary artery disease, heart disease, hypertension, prevention and treatment of left ventricular hypertrophy, myocardial infarction, transient ischaemic attack, peripheral vascular disease, systemic inflammation of the vasculature, septic chock, stroke, cerebral apoplexy, cerebral infarction, cerebral ischaemia, cerebral thrombosis, cerebral embolism, cerebral hemorrhagia, metabolic disorders (e.g. conditions showing reduced metabolic activity or a decrease in resting energy expenditure as a percentage of total fat-free mass, diabetes mellitus, dyslipidemia, fatty liver, gout, hypercholesterolemia, hyperlipidemia, hypertriglyceridemia, hyperuricacidemia, impaired glucose tolerance, impaired fasting glucose, insulin resistance, insulin resistance syndrome, metabolic syndrome, syndrome X, obesity-hypoventilation syndrome (Pickwickian syndrome), type I diabetes, type II diabetes, low HDL- and/or high LDL-cholesterol levels, low adiponectin levels), reproductive and endocrine disorders (e.g. treatment of hypogonadism in males, treatment of infertility or as contraceptive, menstrual abnormalities/emmeniopathy, polycystic ovarian disease, sexual and reproductive dysfunction in women and men (erectile dysfunction), GH-deficient subjects, hirsutism in females, normal variant short stature) and diseases related to the respiratory (e.g. asthma and chronic obstructive pulmonary disease) and gastrointestinal systems (e.g. dysfunction of gastrointestinal motility or intestinal propulsion, diarrhea, emesis, nausea, gallbladder disease, cholelithiasis, obesity-related gastro-esophageal reflux, ulcers).

In a further aspect the present invention provides the use of a compound of formula I in the preparation of a medicament for the treatment or prophylaxis of dermatological disorders, cancers (e.g. colon, rectum, prostate, breast, ovary, endometrium, cervix, gallbladder, bile duct), craniopharyngioma, Prader-Willi syndrome, Turner syndrome, Frohlich's syndrome, glaucoma, infectious diseases, urinary tract disorders and inflammatory disorders (e.g. arthritis deformans, inflammation, inflammatory sequelae of viral encephalitis, osteoarthritis) and orthopedic disorders.

In a still further aspect the present invention provides a method comprising administering a pharmacologically effective amount of a compound of formula I to a patient in need thereof for the prophylaxis or treatment of obesity or being overweight, (e.g., promotion of weight loss and maintenance of weight loss), prevention of weight gain (e.g., medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items), for the treatment of psychiatric disorders such as psychotic and/or mood disorders, schizophrenia and schizo-affective disorder, bipolar disorders, anxiety, anxio-depressive disorders, depression, mania, obsessive-compulsive disorders, impulse control disorders (e.g., Gilles de la Tourette's syndrome), attention disorders like ADD/ADHD, stress, and neurological disorders such as dementia and cognitive and/or memory dysfunction (e.g., amnesia, Alzheimer's disease, Pick's dementia, dementia of ageing, vascular dementia, mild cognitive impairment, age-related cognitive decline, and mild dementia of ageing), neurological and/or neurodegenerative disorders (e.g. Multiple Sclerosis, Raynaud's syndrome, Parkinson's disease, Huntington's chorea and Alzheimer's disease), demyelinisation-related disorders, neuroinflammatory disorders (e.g., Guillain-Barré syndrome).

In a still further aspect the present invention provides a method comprising administering a pharmacologically effective amount of a compound of formula I to a patient in need thereof for the prophylaxis or treatment of dependence and addictive disorders and behaviours (e.g., alcohol and/or drug abuse, pathological gambling, kleptomania), drug withdrawal disorders (e.g., alcohol withdrawal with or without perceptual disturbances; alcohol withdrawal delirium; amphetamine withdrawal; cocaine withdrawal; nicotine withdrawal; opioid withdrawal; sedative, hypnotic or anxiolytic withdrawal with or without perceptual disturbances; sedative, hypnotic or anxiolytic withdrawal delirium; and withdrawal symptoms due to other substances), alcohol and/or drug-induced mood, anxiety and/or sleep disorder with onset during withdrawal, and alcohol and/or drug relapse.

In a still further aspect the present invention provides a method comprising administering a pharmacologically effective amount of a compound of formula I to a patient in need thereof for the prophylaxis or treatment of neurological dysfunctions such as dystonias, dyskinesias, akathisia, tremor and spasticity, treatment of spinal cord injury, neuropathy, migraine, vigilance disorders, sleep disorders (e.g., disturbed sleep architecture, sleep apnea, obstructive sleep apnea, sleep apnea syndrome), pain disorders, cranial trauma.

In a still further aspect the present invention provides a method comprising administering a pharmacologically effective amount of a compound of formula I to a patient in need thereof for the prophylaxis or treatment of immune, cardiovascular disorders (e.g. atherosclerosis, arteriosclerosis, angina pectoris, abnormal heart rhythms, and arrhythmias, congestive heart failure, coronary artery disease, heart disease, hypertension, prevention and treatment of left ventricular hypertrophy, myocardial infarction, transient ischaemic attack, peripheral vascular disease, systemic inflammation of the vasculature, septic chock, stroke, cerebral apoplexy, cerebral infarction, cerebral ischaemia, cerebral thrombosis, cerebral embolism, cerebral hemorrhagia, metabolic disorders (e.g. conditions showing reduced metabolic activity or a decrease in resting energy expenditure as a percentage of total fat-free mass, diabetes mellitus, dyslipidemia, fatty liver, gout, hypercholesterolemia, hyperlipidemia, hypertriglyceridemia, hyperuricacidemia, impaired glucose tolerance, impaired fasting glucose, insulin resistance, insulin resistance syndrome, metabolic syndrome, syndrome X, obesity-hypoventilation syndrome (Pickwickian syndrome), type I diabetes, type II diabetes, low HDL- and/or high LDL-cholesterol levels, low adiponectin levels), reproductive and endocrine disorders (e.g. treatment of hypogonadism in males, treatment of infertility or as contraceptive, menstrual abnormalities/emmeniopathy, polycystic ovarian disease, sexual and reproductive dysfunction in women and men (erectile dysfunction), GH-deficient subjects, hirsutism in females, normal variant short stature) and diseases related to the respiratory (e.g. asthma and chronic obstructive pulmonary disease) and gastrointestinal systems (e.g. dysfunction of gastrointestinal motility or intestinal propulsion, diarrhea, emesis, nausea, gallbladder disease, cholelithiasis, obesity-related gastro-esophageal reflux, ulcers).

In a still further aspect the present invention provides a method comprising administering a pharmacologically effective amount of a compound of formula I to a patient in need thereof for the prophylaxis or treatment of dermatological disorders, cancers (e.g. colon, rectum, prostate, breast, ovary, endometrium, cervix, gallbladder, bile duct), craniopharyngioma, Prader-Willi syndrome, Turner syndrome, Frohlich's syndrome, glaucoma, infectious diseases, urinary tract disorders and inflammatory disorders (e.g. arthritis deformans, inflammation, inflammatory sequelae of viral encephalitis, osteoarthritis) and orthopedic disorders.

The compounds of the present invention are particularly suitable for the treatment of obesity or being overweight, (e.g., promotion of weight loss and maintenance of weight loss), prevention or reversal of weight gain (e.g., rebound, medication-induced or subsequent to cessation of smoking), for modulation of appetite and/or satiety, eating disorders (e.g. binge eating, anorexia, bulimia and compulsive), cravings (for drugs, tobacco, alcohol, any appetizing macronutrients or non-essential food items).

The compounds of formula (I) are useful for the treatment of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, and neurological disorders such as dementia, neurological disorders (e.g. Multiple Sclerosis), Raynaud's syndrome, Parkinson's disease, Huntington's chorea and Alzheimer's disease. The compounds are also potentially useful for the treatment of immune, cardiovascular, reproductive and endocrine disorders, septic shock and diseases related to the respiratory and gastrointestinal systems (e.g. diarrhea). The compounds are also potentially useful as agents in treatment of extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms. The compounds may also eliminate the increase in weight that normally accompanies the cessation of smoking.

In another aspect the present invention provides a compound of formula I as previously defined for use as a medicament.

In a further aspect the present invention provides the use of a compound of formula I in the preparation of a medicament for the treatment or prophylaxis of obesity, psychiatric disorders such as psychotic disorders, schizophrenia, bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms.

In a still further aspect the present invention provides a method of treating obesity, psychiatric disorders such as psychotic disorders such as schizophrenia and bipolar disorders, anxiety, anxio-depressive disorders, depression, cognitive disorders, memory disorders, obsessive-compulsive disorders, anorexia, bulimia, attention disorders like ADHD, epilepsy, and related conditions, neurological disorders such as dementia, neurological disorders (e.g. Multiple Sclerosis), Parkinson's Disease, Huntington's Chorea and Alzheimer's Disease, immune, cardiovascular, reproductive and endocrine disorders, septic shock, diseases related to the respiratory and gastrointestinal systems (e.g. diarrhea), and extended abuse, addiction and/or relapse indications, e.g. treating drug (nicotine, ethanol, cocaine, opiates, etc) dependence and/or treating drug (nicotine, ethanol, cocaine, opiates, etc) withdrawal symptoms comprising administering a pharmacologically effective amount of a compound of formula I to a patient in need thereof.

The compounds of the present invention are particularly suitable for the treatment of obesity, e.g. by reduction of appetite and body weight, maintenance of weight reduction and prevention of rebound.

The compounds of the present invention may also be used to prevent or reverse medication-induced weight gain, e.g. weight gain caused by antipsychotic (neuroleptic) treatment(s). The compounds of the present invention may also be used to prevent or reverse weight gain associated with smoking cessation.

The compounds of the present invention are suitable for use in treating the above indications in juvenile or adolescent patient populations.

Combination Therapy

The compounds of the invention may be combined with another therapeutic agent that is useful in the treatment of obesity such as other anti-obesity drugs, that affect energy expenditure, glycolysis, gluconeogenesis, glucogenolysis, lipolysis, lipogenesis, fat absorption, fat storage, fat excretion, hunger and/or satiety and/or craving mechanisms, appetite/motivation, food intake, or G-I motility.

The compounds of the invention may further be combined with another therapeutic agent that is useful in the treatment of disorders associated with obesity such as hypertension, hyperlipidaemias, dyslipidaemias, diabetes, sleep apnea, asthma, heart disorders, atherosclerosis, macro and micro vascular diseases, liver steatosis, cancer, joint disorders, and gallbladder disorders. For example, a compound of the present invention may be used in combination with a another therapeutic agent that lowers blood pressure or that decreases the ratio of LDL:HDL or an agent that causes a decrease in circulating levels of LDL-cholesterol. In patients with diabetes mellitus the compounds of the invention may also be combined with therapeutic agents used to treat complications related to micro-angiopathies.

The compounds of the invention may be used alongside other therapies for the treatment of obesity and its associated complications the metabolic syndrome and type 2 diabetes, these include biguanide drugs, insulin (synthetic insulin analogues) and oral antihyperglycemics (these are divided into prandial glucose regulators and alpha-glucosidase inhibitors). In another aspect of the invention, the compound of formula I, or a pharmaceutically acceptable salt thereof may be administered in association with a PPAR modulating agent. PPAR modulating agents include but are not limited to a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art.

In addition the combination of the invention may be used in conjunction with a sulfonylurea. The present invention also includes a compound of the present invention in combination with a cholesterol-lowering agent. The cholesterol-lowering agents referred to in this application include but are not limited to inhibitors of HMG-CoA reductase (3-hydroxy-3-methylglutaryl coenzyme A reductase). Suitably the HMG-CoA reductase inhibitor is a statin.

In the present application, the term "cholesterol-lowering agent" also includes chemical modifications of the HMG-CoA reductase inhibitors, such as esters, prodrugs and metabolites, whether active or inactive.

The present invention also includes a compound of the present invention in combination with an inhibitor of the ileal bile acid transport system (IBAT inhibitor). The present invention also includes a compound of the present invention in combination with a bile acid binding resin.

The present invention also includes a compound of the present invention in combination with a bile acid sequestering agent, for example colestipol or cholestyramine or cholestagel.

According to an additional further aspect of the present invention there is provided a combination treatment comprising the administration of an effective amount of a compound of the formula I, or a pharmaceutically acceptable salt thereof, optionally together with a pharmaceutically acceptable diluent or carrier, with the simultaneous, sequential or separate administration one or more of the following agents selected from:

a CETP (cholesteryl ester transfer protein) inhibitor;
a cholesterol absorption antagonist;
a MTP (microsomal transfer protein) inhibitor;
a nicotinic acid derivative, including slow release and combination products;
a phytosterol compound;
probucol;
an anti-coagulant;
an omega-3 fatty acid;
another anti-obesity compound for example sibutramine, phentermine, orlistat, bupropion, ephedrine, thyroxine;
an antihypertensive compound for example an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, an AT-1 blocker, a saluretic, a diuretic or a vasodilator;
a melanin concentrating hormone (MCH) modulator;
an NPY receptor modulator;
an orexin receptor modulator;
a phosphoinositide-dependent protein kinase (PDK) modulator; or
modulators of nuclear receptors for example LXR, FXR, RXR, GR, ERRα, β, PPARα, β, γ and RORalpha;
a monoamine transmission-modulating agent, for example a selective serotonin reuptake inhibitor (SSRI), a noradrenaline reuptake inhibitor (NARI), a noradrenaline-serotonin reuptake inhibitor (SNRI), a monoamine oxidase inhibitor (MAOI), a tricyclic antidepressive agent (TCA), a noradrenergic and specific serotonergic antidepressant (NaSSA);
an antipsychotic agent for example olanzapine and clozapine;
a serotonin receptor modulator;
a leptin/leptin receptor modulator;
a ghrelin/ghrelin receptor modulator;
a DPP-IV inhibitor;
or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula I, or a pharmaceutically acceptable salt thereof, optionally together with a pharmaceutically acceptable diluent or carrier, with the simultaneous, sequential or separate administration of very low calorie diets (VLCD) or low-calorie diets (LCD).

Therefore in an additional feature of the invention, there is provided a method for the treatment of obesity and its associated complications in a warm-blooded animal, such as man, in need of such treatment which comprises administering to said animal an effective amount of a compound of formula I, or a pharmaceutically acceptable salt thereof in simultaneous, sequential or separate administration with an effective amount of a compound from one of the other classes of compounds described in this combination section, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula I, or a pharmaceutically acceptable salt thereof in simultaneous, sequential or separate administration with an effective amount of a compound from one of the other classes of compounds described in this combination section or a pharmaceutically acceptable salt, solvate, solvate of such a salt or a prodrug thereof.

According to a further aspect of the invention there is provided a pharmaceutical composition which comprises a compound of formula I, or a pharmaceutically acceptable salt thereof, and a compound from one of the other classes of compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula I, or a pharmaceutically acceptable salt thereof, and a compound from one of the other classes of compounds described in this combination section or a pharmaceutically acceptable salt, solvate, solvate of such a salt or a prodrug thereof.

According to a further aspect of the present invention there is provided a kit comprising:
a) a compound of formula I, or a pharmaceutically acceptable salt thereof, in a first unit dosage form;
b) a compound from one of the other classes of compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula I, or a pharmaceutically acceptable salt thereof, together with a pharmaceutically acceptable diluent or carrier, in a first unit dosage form;
b) a compound from one of the other classes of compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula I, or a pharmaceutically acceptable salt thereof, and one of the other compounds described in this combination section, or a pharmaceutically acceptable salt, solvate, solvate of such a salt or a prodrug thereof, in the manufacture of a medicament for use in the the treatment of obesity and its associated complications in a warm-blooded animal, such as man.

According to another feature of the invention there is provided the use of a compound of the formula I, or a pharmaceutically acceptable salt thereof, and one of the other compounds described in this combination section, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula I, or a pharmaceutically acceptable salt thereof, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Furthermore, a compound of the invention may also be combined with therapeutic agents that are useful in the treatment of disorders or conditions associated with obesity (such as type II diabetes, metabolic syndrome, dyslipidemia, impaired glucose tolerance, hypertension, coronary heart disease, non-alcoholic steatohepatitis, osteoarthritis and some cancers) and psychiatric and neurological conditions.

It will be understood that there are medically accepted definitions of obesity and being overweight. A patient may be identified by, for example, measuring body mass index (BMI), which is calculated by dividing weight in kilograms by height in metres squared, and comparing the result with the definitions.

Pharmacological Activity

Compounds of the present invention are active against the receptor product of the CB1 gene. The affinity of the compounds of the invention for central cannabinoid receptors is demonstrable in methods described in Devane et al, Molecular Pharmacology, 1988, 34,605 or those described in WO01/70700 or EP 656354. Alternatively the assay may be performed as follows.

10 μg of membranes prepared from cells stably transfected with the CB1 gene were suspended in 200 μl of 100 mM NaCl, 5 mM $MgCl_2$, 1 mM EDTA, 50 mM HEPES (pH 7.4), 1 mM DTT, 0.1% BSA and 100 μM GDP. To this was added an EC80 concentration of agonist (CP55940), the required concentration of test compound and 0.1 μCi [$^{35}$S]-GTPγS.

The reaction was allowed to proceed at 30° C. for 45 min. Samples were then transferred on to GF/B filters using a cell harvester and washed with wash buffer (50 mM Tris (pH 7.4), 5 mM $MgCl_2$, 50 mM NaCl). Filters were then covered with scintillant and counted for the amount of [$^{35}$S]-GTPγS retained by the filter.

Activity is measured in the absence of all ligands (minimum activity) or in the presence of an EC80 concentration of CP55940 (maximum activity). These activities are set as 0% and 100% activity respectively. At various concentrations of novel ligand, activity is calculated as a percentage of the maximum activity and plotted. The data are fitted using the equation y=A+((B−A)/1+((C/x) UD)) and the IC50 value determined as the concentration required to give half maximal inhibition of GTPγS binding under the conditions used.

The compounds of the present invention are active at the CB1 receptor (IC50<1 micromolar). Most preferred compounds have IC50<200 nanomolar. For example the IC50 of Example 1 is 18 nM and Example 2 is 28 nM The compounds of the invention are believed to be selective CB1 antagonists or inverse agonists. The potency, selectivity profile and side effect propensity may limit the clinical usefulness of hitherto known compounds with alleged CB1 antagonistic/inverse agonistic properties. In this regard, preclinical evaluation of compounds of the present invention in models of gastrointestinal and/or cardiovascular function indicates that they offer significant advantages compared to representative reference CB1 antagonist/inverse agonist agents.

The compounds of the present invention may provide additional benefits in terms of potency, selectivity profile, bioavailability, half-life in plasma, blood brain permeability, plasma protein binding (for example increasing the free fraction of drug) or solubility compared to representative reference CB1 antagonists/inverse agonist agents.

The utility of the compounds of the present invention in the treatment of obesity and related conditions is demonstrated by a decrease in body weight in cafeteria diet-induced obese mice. Female C57B1/6J mice were given ad libitum access to calorie-dense 'cafeteria' diet (soft chocolate/cocoa-type pastry, chocolate, fatty cheese and nougat) and standard lab chow for 8-10 weeks. Compounds to be tested were then administered systemically (iv, ip, sc or po) once daily for a minimum of 5 days, and the body weights of the mice monitored on a daily basis. Simultaneous assessment of adiposity was carried by means of DEXA imaging at baseline and termination of the study. Blood sampling was also carried out to assay changes in obesity-related plasma markers.

EXAMPLES

Abbreviations

DMF dimethylformamide
DEA Diethylamine
EtOAc ethyl acetate
THF tetrahydrofuran
TLC thin layer chromatography
t triplet
s singlet
d doublet
q quartet
qvint quintet
m multiplet
br broad
bs broad singlet
dm doublet of multiplet
bt broad triplet
dd doublet of doublet
General Experimental Procedures Mass spectra were recorded on either a Micromass ZQ single quadrupole or a Micromass LCZ single quadrupole mass spectrometer both equipped with a pneumatically assisted electrospray interface (LC-MS). $^1$H NMR measurements were performed on either a Varian Mercury 300 or a Varian Inova 500, operating at $^1$H frequencies of 300 and 500 MHz respectively. Chemical shifts are given in ppm with $CDCl_3$ as internal standard. $CDCl_3$ is used as the solvent for NMR unless otherwise stated. Purification was performed on a semipreparative HPLC with a mass triggered fraction collector, Shimadzu QP 8000 single quadrupole mass spectrometer equipped with 19×100 mm C8 column. The mobile phase used was, if nothing else is stated, acetonitrile and buffer (0.1 M $NH_4Ac$:acetonitrile 95:5).

For isolation of isomers, a Kromasil CN E9344 (250×20 mm i.d.) column was used. Heptane:ethyl acetate:DEA 95:5: 0.1 was used as mobile phase (1 ml/min). Fraction collection was guided using a UV-detector (330 nm).

Examples of the Invention

Example 1

Step 1

N-(4-Benzyloxyphenyl)-2,4-dichloro-benzamidine

4-Benzyloxyaniline hydrochloride (5.0 g, 21.2 mmol) was dropwise added to a solution of ethylmagnesium bromide (44.5 ml, 1M in THF, 44.5 mmol) in 25 ml dry THF under nitrogen atmosphere. After stirring for 20 minutes a solution of 2,4-dichlorobenzonitrile (3.65 g, 21.2 mmol) in 25 ml THF was added. The reaction mixture was stirred for 20 hours at room temperature. Water (50 ml) was carefully added. Extraction with EtOAc (2×100 ml), drying (Na$_2$SO$_4$), filtration and evaporation to dryness afforded 7.7 g (98%) of the title compound.

Step 2

1-(4-Benzyloxyphenyl)-2-(2,4-dichlorophenyl)-5-methyl-1H-imidazole-4-carboxylic acid ethyl ester To N-(4-benzyloxyphenyl)-2,4-dichlorobenzamidine, from Ex. 1, Step 1 (6.88 g, 18.5 mmol) dissolved in 50 ml THF was added potassium carbonate (2.56 g, 18.5 mmol) and the suspension was stirred for 10 minutes. Ethyl-3-bromo-2-oxobutanoate (4.65 g, 22.2 mmol) was dropwise added over 1 hour, and the mixture was stirred for 66 hours at room temperature. The solution was filtered and evaporated to dryness. The residue was dissolved in acetic acid and refluxed for 1 hour. The mixture was cooled to room temperature, 100 ml water added and the product extracted with EtOAc (2×200 ml). The combined organic phases were washed with saturated sodium hydrogen carbonate, dried (Na$_2$SO$_4$), filtered and concentrated. Flash chromatography (silica, hexane:EtOAc 70:30, 60:40) afforded 5.75 g (65%) of the title compound as a pale yellow solid.

1H NMR (CDCl$_3$): δ 7.5-7.2 (8H, m), 7.1-6.9 (4H, m), 5.1 (2H, s), 4.5 (2H, q), 2.5 (3H, s), 1.5 (3H, t), MS m/z 504 (M+Na), 985 (2 M+Na)

Step 3

1-(4-Benzyloxyphenyl)-2-(2,4-dichlorophenyl)-5-methyl-1H-imidazole-4-carboxylic acid To a suspension of 1-(4-benzyloxyphenyl)-2-(2,4-dichlorophenyl)-5-methyl-1H-imidazole-4-carboxylic acid ethyl ester, from Ex. 1, Step 2 (3.62 g, 7.5 mmol) in 60 ml methanol was added potassium hydroxide (4.05 g, 72 mmol) in water (20 ml), and the reaction mixture was refluxed for 2 hours. The mixture was cooled to room temperature, acidified to pH~2 with 1 M HCl and extracted with ethyl acetate (2×200 ml). The combined organic phases were dried (Na$_2$SO$_4$), filtered and concentrated to give 3.38 g (99%) of the title compound.

Step 4

1-(4-Benzyloxyphenyl)-2-(2,4-dichlorophenyl)-5-methyl-1H-imidazole-4-carboxylic acid piperidin-1-ylamide A solution of 1-(4-benzyloxyphenyl)-2-(2,4-dichlorophenyl)-5-methyl-1H-imidazole-4-carboxylic acid, from Ex 1, Step 3 (3.38 g, 7.5 mmol) in 60 ml CH$_2$Cl$_2$ was added 3 drops of DMF followed by oxalyl chloride (1.3 ml, 14.9 mmol). The mixture was refluxed for 2 hours, cooled to room temperature and evaporated to dryness. The residue was dissolved in 50 ml CH$_2$Cl$_2$ and cooled to 0° C. Triethylamine (2.1 ml, 14.9 mmol) was added followed by 1-aminopiperidine (0.9 ml, 8.2 mmol) and the mixture was stirred at room temperature for 2 hours. Water (300 ml) was added, the mixture extracted with CH$_2$Cl$_2$ (3×100 ml), dried (Na$_2$SO$_4$), filtered and concentrated. Flash chromatography (silica, hexane:EtOAc 1:2, EtOAc) afforded 2.94 g (74%) of the title compound as a white solid.

$^1$H NMR (CDCl$_3$): δ 7.5-7.2 (8H, m), 7.1-6.9 (4H, m), 5.1 (2H, s), 3.0-2.7 (4H, m), 2.5 (3H, s), 1.9-1.7 (4H, m), 1.6-1.4 (2H, m). NIS m/z 558 (M+Na). HPLC: 96.5%.

Example 2

Step 1

2-(2,4-Dichlorophenyl)-1-(4-hydroxyphenyl)-5-methyl-1H-imidazole-4-carboxylic acid piperidin-1-ylamide 1-(4-Benzyloxyphenyl)-2-(2,4-dichlorophenyl)-5-methyl-1H-imidazole-4-carboxylic acid piperidin-1-ylamide, from Ex. 1, Step 4 (2.78 g, 5.2 mmol) was dissolved in 80 ml CH$_2$Cl$_2$ and cooled to 0° C. Boron tribromide solution (1 M in CH$_2$Cl$_2$, 10.4 ml, 10.4 mmol) was added dropwise and the reaction mixture was stirred at room temperature for 1 hour. Water (200 ml) was added and the solution extracted with EtOAc (3×200 ml). The combined organic phases were dried (Na$_2$SO$_4$), filtered and concentrated. Flash chromatography (silica, hexane:EtOAc 1:3, EtOAc) afforded 1.34 g (58%) of the title compound as a white solid.

$^1$H NMR (CDCl$_3$): δ 8.6 (1H, bs), 7.4-7.1 (3H, m), 7.0-6.9 (4H, m), 3.0-2.8 (4H, m), 2.5 (3H, s), 1.8-1.6 (4H, m), 1.5-1.3 (2H, m).

Step 2

Ethanesulfonic acid 4-[2-(2,4-dichlorophenyl)-5-methyl-4-(piperidin-1-ylcarbamoyl)-imidazol-1-yl]-phenyl ester A solution of 2-(2,4-dichlorophenyl)-1-(4-hydroxyphenyl)-5-methyl-1H-imidazole-4-carboxylic acid piperidin-1-ylamide, from Ex. 2, Step 1 (321 mg, 0.72 mmol) in 10 ml CH$_2$Cl$_2$ was cooled to 0° C. Triethylamine (101 μl, 0.72 mmol) was added followed by ethanesulfonyl chloride (69 μl, 0.72 mmol) and the reaction mixture was stirred at room temperature overnight. Water was added, the mixture extracted with CH$_2$Cl$_2$ (3×20 ml), dried (Na$_2$SO$_4$), filtered and concentrated. Flash chromatography (silica, hexane:EtOAc 1:3) afforded 230 mg (60%) of the title compound as a white solid.

$^1$H NMR (CDCl$_3$): δ 7.9 (1H, broad s), 7.4-7.1 (7H, m), 3.3 (2H, q), 3.0-2.8 (4H, m), 2.5 (3H, s), 1.9-1.7 (4H, m), 1.5 (3H, t), 1.5-1.4 (2H, m). MS m/z 560 (M+Na). HPLC: 97.0%.

Example 3

Propane-1-sulfonic acid 4-[2-(2,4-dichlorophenyl)-5-methyl-4-(piperidin-1-ylcarbamoyl)-imidazol-1-yl] phenyl ester A solution of 2-(2,4-dichlorophenyl)-1-(4-hydroxyphenyl)-5-methyl-1H-imidazole-4-carboxylic acid piperidin-1-ylamide, from Ex. 2, Step 1 (320 mg, 0.72 mmol) in 10 ml CH$_2$Cl$_2$ was cooled to 0° C. Triethylamine (100 μl, 0.72 mmol) was added followed by 1-propanesulfonyl chloride (81 μl, 0.72 mmol) and the reaction mixture was stirred at room temperature overnight. Water was added, the mixture extracted with CH$_2$Cl$_2$ (3×20 ml), dried (Na$_2$SO$_4$), filtered and concentrated. Flash chromatography (silica, hexane:EtOAc 1:2) afforded 220 mg (56%) of the title compound as a white solid.

¹H NMR (CDCl₃): δ 7.9 (1H, broad s), 7.4-7.1 (7H, m), 3.3 (2H, m), 3.0-2.8 (4H, m), 2.5 (3H, s), 2.1-1.9 (2H, m), 1.9-1.7 (4H, m), 1.5-1.4 (2H, m), 1.2 (3H, t). MS m/z 574 (M+Na). HPLC: 97.0%.

Example 4

Butane-1-sulfonic acid 4-[2-(2,4-dichlorophenyl)-5-methyl-4-(piperidin-1-ylcarbamoyl)-imidazol-1-yl]phenyl ester A solution of 2-(2,4-dichlorophenyl)-1-(4-hydroxyphenyl)-5-methyl-1H-imidazole-4-carboxylic acid piperidin-1-ylamide, Ex. 2, Step 1 (320 mg, 0.72 mmol) in 10 ml CH₂Cl₂ was cooled to 0° C. Triethylamine (100 μl, 0.72 mmol) was added followed by 1-butanesulfonyl chloride (93 μl, 0.72 mmol) and the reaction mixture was stirred at room temperature overnight. Water was added and the mixture extracted with CH₂Cl₂ (3×20 ml), dried (Na₂SO₄), filtered and concentrated. Flash chromatography (silica, hexane:EtOAc 1:2) afforded 230 mg (57%) of the title compound as a white solid.

¹H NMR (CDCl₃): δ 7.9 (1H, bs), 7.4-7.1 (7H, m), 3.3 (2H, m), 3.0-2.8 (4H, m), 2.5 (3H, s), 2.1-1.9 (2H, m), 1.9-1.7 (4H, m), 1.6-1.4 (4H, m), 1.0 (3H, t) MS m/z 588 (M+Na). HPLC: 96.0%.

Example 5

2-(2,4-Dichlorophenyl)-5-methyl-1-[4-(4,4,4-trifluorobutoxy)-phenyl]-1H-imidazole-4-carboxylic acid piperidin-1-ylamide 1-Iodo-4,4,4-trifluorobutane (376 mg, 1.58 mmol) was added dropwise to a suspension of 2-(2,4-dichlorophenyl)-1-(4-hydroxyphenyl)-5-methyl-1H-imidazole-4-carboxylic acid piperidin-1-ylamide, from Ex 2, Step 1 (351 mg, 0.79 mmol) and K₂CO₃ (218 mg, 1.58 mmol) in 50 ml acetone. The reaction mixture was refluxed overnight, cooled, filtered and concentrated. Flash chromatography (silica, hexane:EtOAc 1:2) afforded 200 mg (46%) of the title compound as a white solid.

¹H NMR (CDCl₃): δ 8.0 (1H, broad s), 7.4-7.2 (3H, m), 7.1-7.0 (2H, m), 6.9-6.8 (2H, m), 4.1-4.0 (2H, m), 3.0-2.9 (4H, m), 2.5-2.2 (5H, m), 2.2-2.0 (2H, m), 1.9-1.7 (4H, m), 1.6-1.4 (2H, m). MS m/z 578 (M+Na). HPLC: 99.4%.

Example 6

3,3,3-Trifluoropropane-1-sulfonic acid 4-[2-(2,4-dichlorophenyl)-5-methyl-4-(piperidin-1-ylcarbamoyl)imidazol-1-yl]phenyl ester 2-(2,4-Dichlorophenyl)-1-(4-hydroxyphenyl)-5-methyl-1H-imidazole-4-carboxylic piperidin-1-ylamide, from Ex 2, Step 1, (0.89 g, 2.00 mmol) was dissolved in dichloromethane (20 ml), cooled to 0° C. and triethylamine (0.35 ml, 2.4 mmol) added followed by 3,3,3-trifluoropropanesulfonyl chloride (prepared by an analogous method to that described in WO00/010968 for the butyl homologue) (0.35 ml, 2.40 mmol). The reaction mixture was stirred at room temperature overnight. TLC showed remaining starting material and so another portion of triethylamine and 3,3,3-trifluoropropanesulfonyl chloride was added and the reaction mixture stirred for additional 2 hrs. Water was added and the product was extracted with dichloromethane, dried (Na₂SO₄), filtered and concentrated. Flash chromatography (hexane:EtOAc 1:3-EtOAc) followed by recrystallization (hexane:EtOAc) afforded 700 mg (59%) of the title compound as a colorless solid.

¹H NMR(CDCl₃): δ 7.40-7.10 (8H, m), 3.60-3.43 (2H, m), 3.02-2.70 (6H, m), 2.50 (3H, s), 1.92-1.70 (4H, m), 1.57-1.40 (2H, m). MS m/z 627 (M+Na). HPLC: 97.8%

Example 7

4,4,4-Trifluorobutane-1-sulfonic acid 4-[2-(2,4-dichlorophenyl)-5-methyl-4-(piperidin-1-ylcarbamoyl)imidazol-1-yl]-phenyl ester 2-(2,4-Dichlorophenyl)-1-(4-hydroxyphenyl)-5-methyl-1H-imidazole-4-carboxylic piperidin-1-ylamide, from Ex 2, Step 1 (0.49 g, 1.20 mmol) was dissolved in dichloromethane (20 ml), cooled to 0° C. and triethylamine (0.67 ml, 4.8 mmol) added followed by 4,4,4-trifluorobutane-1-sulfonyl chloride (prepared as described in WO00/010968) (0.38 g, 1.80 mmol). The reaction mixture was stirred at room temperature for 3 hrs. TLC showed remaining starting material and another portion of triethylamine and 4,4,4-trifluorobutane-1-sulfonyl chloride was added and the reaction mixture stirred overnight. Water was added, the product extracted with dichloromethane, dried (Na₂SO₄), filtered and concentrated. Flash chromatography (hexane:EtOAc 1:3-EtOAc) followed by recrystallization (hexane:EtOAc) afforded 0.45 g (61%) of the title compound as a colorless solid.

¹H NMR(CDCl₃): δ 7.35-7.19 (8H, m), 3.40 (2H, m), 3.05-2.90 (4H, m), 2.78-2.20 (7H, s and m), 1.92-1.70 (4H, m), 1.57-1.40 (2H, m). MS m/z 641 (M+Na). HPLC: 98.6%

Example 8

4-{2-(2,4-dichlorophenyl)-5-methyl-4-[(piperidin-1-ylamino)carbonyl]-1H-imidazol-1-yl}phenyl thiophene-2-sulfonate 2-(2,4-Dichlorophenyl)-1-(4-hydroxyphenyl)-5-methyl-N-piperidin-1-yl-1H-imidazole-4-carboxamide, prepared as described in Ex. 2, Step 1 (100 mg, 0.22 mmol) and triethylamine (0.31 ml, 2.25 mmol) in dichloromethane (2.5 ml) were cooled to −78° C. 2-Thiophenesulfonyl chloride (287 mg, 1.57 mmol) dissolved in dichloromethane (2.5 ml) was carefully added to the reaction mixture. The resulting mixture was stirred at −78° C. for 1 h, and at room temperature overnight. Water was added to the reaction, the phases were separated and the organic phase washed with water and dried. The solvent was removed under reduced pressure and separation by preparatory HPLC gave the title compound (110 mg, 83%) as a solid.

¹H NMR (400 MHz) δ 7.89 (s, NH), 7.75-7.74 (m, 1H), 7.55-7.54 (m, 1H), 7.35-7.34 (m, 1H), 7.30-7.25 (m, 2H), 7.13-7.11 (m, 1H), 7.07 (d, 4H), 2.90-2.86 (m, 4H), 1.80-1.75 (m, 4H), 1.48-1.42 (m, 2H). MS m/z 591 (M+H)⁺.

Example 9

4-{2-(2,4-dichlorophenyl)-5-methyl-4-[(piperidin-1-ylamino)carbonyl]-1H-imidazol-1-yl}phenyl pyridine-3-sulfonate 2-(2,4-Dichlorophenyl)-1-(4-hydroxyphenyl)-5-methyl-N-piperidin-1-yl-1H-imidazole-4-carboxamide, prepared as described in Ex. 2, Step 1 (100 mg, 0.22 mmol) and triethylamine (0.31 ml, 2.25 mmol) in dichloromethane (5.0 ml) were cooled to −78° C. 3-Pyridinesulfonyl chloride (144 mg, 0.67 mmol) was added in small portions to the reaction mixture. The resulting mixture was stirred at −78° C. for 1 h, and at room temperature overnight. Water was added to the reaction, the phases were separated and the organic phase washed with water and dried. The solvent was removed under reduced pressure and separation by preparatory HPLC gave the title compound (110 mg, 84%) as a solid.

$^1$H NMR (400 MHz) δ 8.96 (s, 1H), 8.92 (s, 1H), 8.09-8.06 (m, 1H), 7.89 (s, 1H), 7.51-7.49 (m, 1H), 7.36 (d, 1H), 7.30-7.25 (m, 2H), 7.06 (s, 4H), 2.88-2.84 (m, 4H), 2.48 (s, 3H), 1.79-1.74 (m, 4H), 1.47-1.41 (m, 2H). MS m/z 586 (M+H)$^+$.

Example 10

4-{2-(2,4-dichlorophenyl)-5-methyl-4-[(piperidin-1-ylamino)carbonyl]-1H-imidazol-1-yl}phenyl 5-chlorothiophene-2-sulfonate 2-(2,4-Dichlorophenyl)-1-(4-hydroxyphenyl)-5-methyl-N-piperidin-1-yl-1H-imidazole-4-carboxamide, prepared as described in Ex. 2, Step 1 (100 mg, 0.22 mmol) and triethylamine (0.16 ml, 1.12 mmol) in dichloromethane (2.5 ml) were cooled to −78° C. 5-Chlorothiophen-2-sulfonyl chloride (244 mg, 1.12 mmol) in dichloromethane (2.5 ml) was carefully added to the reaction mixture. The resulting mixture was stirred at −78° C. for 1 h, and at room temperature overnight. Water was added to the reaction, the phases were separated and the organic phase washed with water and dried. The solvent was removed under reduced pressure and separation by preparatory HPLC gave the title compound (84 mg, 60%) as a solid.

$^1$H NMR (400 MHz) δ 7.90 (s, NH), 7.34-7.26 (m, 4H), 7.10 (d, 4H), 6.96 (d, 1H), 2.88-2.85 (m, 4H), 2.49 (s, 3H), 1.79-1.74 (m, 4H), 1.47-1.42 (m, 2H). MS m/z 625 (M+H)$^+$.

Example 11

4-{2-(2,4-dichlorophenyl)-5-methyl-4-[(piperidin-1-ylamino)carbonyl]-1H-imidazol-1-yl}phenyl 3-methylbutane-1-sulfonate 2-(2,4-Dichlorophenyl)-1-(4-hydroxyphenyl)-5-methyl-N-piperidin-1-yl-1H-imidazole-4-carboxamide, prepared as described in Ex. 2, Step 1 (50 mg, 0.11 mmol) was dissolved in dichloromethane (3.0 ml), cooled to 0° C. and triethylamine (20 μl, 0.13 mmol) was added to the mixture. The resulting mixture was cooled to −78° C. and 3-methylbutane-1-sulfonyl chloride (23 mg, 0.13 mmol) was carefully added. The reaction was stirred at −78° C. for 1.5 h. Water was added to the reaction, the product extracted with dichloromethane and dried. The solvent was removed under reduced pressure and separation by preparatory HPLC gave the title compound (46 mg, 71%) as a solid.

$^1$H NMR (400 MHz) δ 7.86 (s, NH), 7.30-7.20 (m, 5H), 7.12-7.09 (m, 2H), 3.26-3.22 (m, 2H), 2.86-2.80 (m, 4H), 2.46 (s, 3H), 1.86-1.80 (m, 3H), 1.77-1.69 (m, 4H), 1.45-1.37 (m, 2H), 0.93 (d, 6H). MS m/z 579 (M+H)$^+$.

Example 12

4-{2-(2,4-dichlorophenyl)-5-methyl-4-[(piperidin-1-ylamino)carbonyl]-1H-imidazol-1-yl}phenyl 3,3-dimethylbutane-1-sulfonate 2-(2,4-Dichlorophenyl)-1-(4-hydroxyphenyl)-5-methyl-N-piperidin-1-yl-1H-imidazole-4-carboxamide, prepared as described in Ex. 2, Step 1 (50 mg, 0.11 mmol) was dissolved in dichloromethane (3.0 ml), cooled to 0° C. and triethylamine (20 μl, 0.13 mmol) was added to the mixture. The resulting mixture was cooled to −78° C. and 3,3-dimethylbutane-1-sulfonyl chloride (25 mg, 0.13 mmol) was carefully added. The reaction was stirred at −78° C. for 2 h. Water was added to the reaction, the product extracted with dichloromethane and dried. The solvent was removed under reduced pressure and separation by preparatory HPLC gave the title compound (46 mg, 69%) as a solid.

$^1$H NMR (400 MHz) δ 7.85 (s, NH), 7.30-7.20 (m, 5H), 7.13-7.09 (m, 2H), 3.24-3.18 (m, 2H), 2.86-2.81 (m, 4H), 2.46 (s, 3H), 1.86-1.80 (m, 2H), 1.76-1.69 (m, 5H), 1.44-1.37 (m, 2H), 0.92 (s, 9H). MS m/z 593 (M+H)$^+$.

Example 13

Step 1: 1-[4-(Benzyloxy)phenyl]-2-(2,4-dichlorophenyl)-5-methyl-N-[5-(trifluoromethyl)pyridin-2-yl]-1H-imidazole-4-carboxamide 2-Amino-5-(trifluoromethyl)pyridine (404 mg, 2.49 mmol) was dissolved in dichloromethane (2.5 ml) under argon and trimethylaluminium (1.25 ml, 2.0 M in toluene, 2.5 mmol) was carefully added during 5 min. The solution was stirred at ambient temperature for 1.5 h and, as a result, a 0.66 M solution of an amidation reagent was obtained. 3.75 ml (2.5 mmol) of this stock solution was added to ethyl 1-[4-(benzyloxy)phenyl]-2-(2,4-dichlorophenyl)-5-methyl-1H-imidazole-4-carboxylate, prepared as described in Ex. 1, Step 2, (400 mg, 0.83 mmol) and the reaction solution was stirred at 45° C. overnight. The reaction solution was cooled to 0° C. and quenched with HCl (aq, 2 M, 7.5 ml). The mixture was diluted with dichloromethane and neutralized by addition of KOH (aq, 2 M). The organic phase was separated and the aqueous phase was extracted further with dichloromethane. The collected organic phases were washed with H$_2$O before drying with Na$_2$SO$_4$. The solvent was removed under reduced pressure and purification by preparatory HPLC gave the title compound (319 mg, 64%) as a solid.

$^1$H NMR (400 MHz) δ 9.89 (s, NH), 8.54 (s, 1H), 8.50 (d, 1H), 7.92-7.88 (m, 1H), 7.40-7.33 (m, 5H), 7.27-7.20 (m, 3H), 7.03-6.91 (m, 4H), 5.02 (s, 2H), 2.50 (s, 3H). MS m/z 597 (M+H)$^+$.

Step 2: 2-(2,4-dichlorophenyl)-1-(4-hydroxyphenyl)-5-methyl-N-[5-(trifluoromethylpyridin-2-yl]-1H-imidazole-4-carboxamide 1-[4-(benzyloxy)phenyl]-2-(2,4-dichlorophenyl)-5-methyl-N-[5-(trifluoromethyl)pyridin-2-yl]-1H-imidazole-4-carboxamide (319 mg, 0.53 mmol) was dissolved in hydrogen bromide (7.5 ml, 4.1 M in acetic acid, 30.75 mmol) and the reaction mixture was stirred at room temperature for 4 h. The acetic acid was co-evaporated with ethanol, the residue neutralized with ammonia and dissolved in methanol. Purification by flash chromatography gave the title compound (266 mg, 98%).

$^1$H NMR (400 MHz) δ 10.36 (s, NH el. OH), 10.09 (s, NH el. OH), 8.89 (s, 1H), 8.69 (d, 1H), 8.48-8.43 (m, 1H), 7.87-7.80 (m, 2H), 7.67 (d, 1H), 7.41 (d, 2H), 7.06 (d, 2H), 2.65 (s, 3H). MS m/z 507 (M+H)$^+$.

Step 3: 4-[2-(2,4-dichlorophenyl)-5-methyl-4-({[5-(trifluoromethyl)pyridin-2-yl]amino}carbonyl)-1H-imidazol-1-yl]phenyl 3,3,3-trifluoropropane-1-sulfonate 2-(2,4-dichlorophenyl)-1-(4-hydroxyphenyl)-5-methyl-N-[5-(trifluoromethyl)pyridin-2-yl]-1H-imidazole-4-carboxamide (136 mg, 0.27 mmol) and triethylamine (40 μl, 0.32 mmol) in dichloromethane (4.0 ml) were cooled to −78° C.

3,3,3-trifluoropropane-1-sulfonyl chloride (63 mg, 0.32 mmol) was carefully added to the reaction mixture. The resulting mixture was stirred at −78° C. for 1 h, and then allowed to reach room temperature. Water was added to the reaction, and the phases were separated. The organic phase was washed with NaHCO$_3$, brine and dried with Na$_2$SO$_4$. The solvent was removed under reduced pressure and separation by preparatory HPLC gave the title compound (88 mg, 49%) as a solid.

$^1$H NMR (400 MHz) δ 9.87 (s, NH), 8.55 (s, 1H), 8.49 (d, 1H), 7.93-7.89 (m, 1H), 7.34-7.18 (m, 7H), 3.53 (m, 2H), 2.85-2.73 (m, 2H), 2.54 (s, 3H). MS m/z 667 (M+H)$^+$.

Example 14

4-[2-(2,4-dichlorophenyl)-5-methyl-4-({[5-(trifluoromethyl)pyridin-2-yl]amino}carbonyl)-1H-imidazol-1-yl]phenyl 3-methylbutane-1-sulfonate 2-(2,4-dichlorophenyl)-1-(4-hydroxyphenyl)-5-methyl-N-[5-(trifluoromethyl)pyridin-2-yl]-1H-imidazole-4-carboxamide, prepared as described in Ex. 13, Step 3 (139 mg, 0.27 mmol) and triethylamine (46 μl, 0.33 mmol) in dichloromethane (4.0 ml) were cooled to −78° C. 3-Methylbutane-1-sulfonyl chloride (56 mg, 0.33 mmol) was carefully added to the reaction mixture. The resulting mixture was stirred at −78° C. for 1 h, and then allowed to reach room temperature. Water was added to the reaction, and the phases were separated. The organic phase was washed with NaHCO$_3$, brine and dried with Na$_2$SO$_4$. The solvent was removed under reduced pressure and separation by preparatory HPLC gave the title compound (81 mg, 46%) as a solid.

$^1$H NMR (400 MHz) δ 9.87 (s, NH), 8.55 (s, 1H), 8.49 (d, 1H), 7.93-7.89 (m, 1H), 7.34-7.14 (m, 7H), 3.29-3.24 (m, 2H), 2.53 (s, 3H), 1.88-1.81 (m, 2H), 1.79-1.69 (m, 1H), 0.95 (d, 6H). MS m/z 641 (M+H)$^+$.

General Synthetic Route

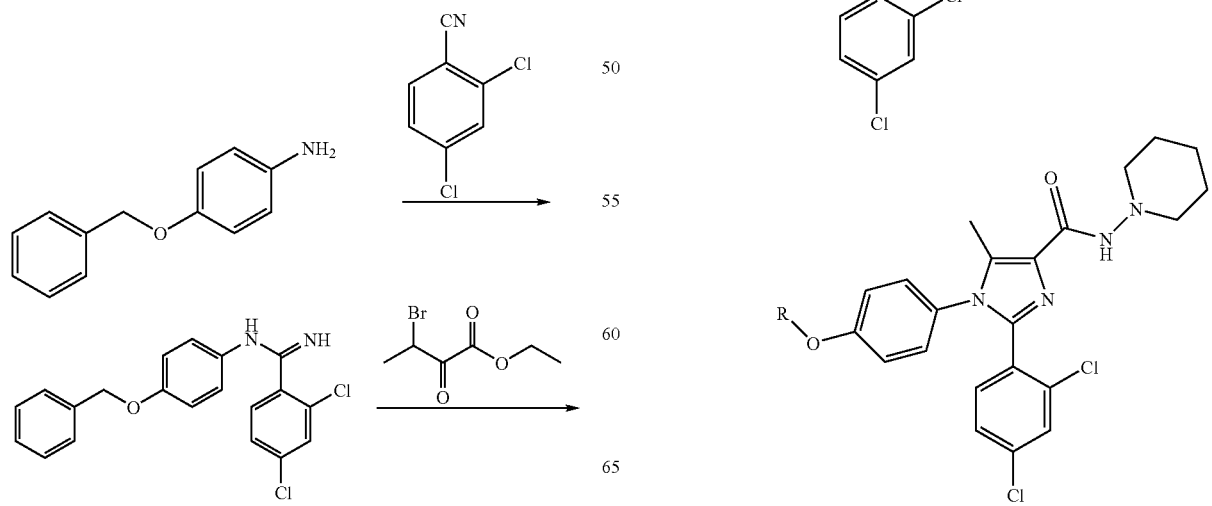

The invention claimed is:

1. A compound selected from one of the following:
   ethanesulfonic acid 4-[2-(2,4-dichlorophenyl)-5-methyl-4-(piperidin-1-ylcarbamoyl)-imidazol-1-yl]phenyl ester;
   propane-1-sulfonic acid 4-[2-(2,4-dichlorophenyl)-5-methyl-4-(piperidin-1-ylcarbamoyl)-imidazol-1-yl]phenyl ester;
   butane-1-sulfonic acid 4-[2-(2,4-dichlorophenyl)-5-methyl-4-(piperidin-1-ylcarbamoyl)-imidazol-1-yl]phenyl ester;
   3,3,3-trifluoropropane-1-sulfonic acid 4-[2-(2,4-dichlorophenyl)-5-methyl-4-(piperidin-1-ylcarbamoyl)imidazol-1-yl]phenyl ester;
   4,4,4-trifluorobutane-1-sulfonic acid 4-[2-(2,4-dichlorophenyl)-5-methyl-4-(piperidin-1-ylcarbamoyl)imidazol-1-yl]phenyl ester;
   4-{2-(2,4-dichlorophenyl)-5-methyl-4-[(piperidin-1-ylamino)carbonyl]-1H-imidazol-1-yl}phenyl 3-methylbutane-1-sulfonate; and
   4-{2-(2,4-dichlorophenyl)-5-methyl-4-[(piperidin-1-ylamino)carbonyl]-1H-imidazol-1-yl}phenyl 3,3-dimethylbutane-1-sulfonate;
   or a pharmaceutically acceptable salt thereof.

2. A pharmaceutical formulation comprising a compound of claim 1 and a pharmaceutically acceptable adjuvant, diluent or carrier.

3. A method of treating obesity comprising administering a pharmacologically effective amount of a compound of claim 1 to a patient in need thereof.

4. A compound according to claim 1 that is propane-1-sulfonic acid 4-[2-(2,4-dichlorophenyl)-5-methyl-4-(piperidin-1-ylcarbamoyl)-imidazol-1-yl]phenyl ester or a pharmaceutically acceptable salt thereof.

5. A compound according to claim 1 that is butane-1-sulfonic acid 4-[2-(2,4-dichlorophenyl)-5-methyl-4-(piperidin-1-ylcarbamoyl)-imidazol-1-yl]phenyl ester or a pharmaceutically acceptable salt thereof.

6. A compound according to claim 1 that is 3,3,3-trifluoropropane-1-sulfonic acid 4-[2-(2,4-dichlorophenyl)-5-methyl-4-(piperidin-1-ylcarbamoyl)imidazol-1-yl]phenyl ester or a pharmaceutically acceptable salt thereof.

7. A compound according to claim 1 that is 4,4,4-trifluorobutane-1-sulfonic acid 4-[2-(2,4-dichlorophenyl)-5-methyl-4-(piperidin-1-ylcarbamoyl)imidazol-1-yl]phenyl ester or a pharmaceutically acceptable salt thereof.

8. A compound according to claim 1 that is 4-{2-(2,4-dichlorophenyl)-5-methyl-4-[(piperidin-1-ylamino)carbonyl]-1H-imidazol-1-yl}phenyl 3-methylbutane-1-sulfonate or a pharmaceutically acceptable salt thereof.

9. A compound according to claim 1 that is 4-{2-(2,4-dichlorophenyl)-5-methyl-4-[(piperidin-1-ylamino)carbonyl]-1H-imidazol-1-yl}phenyl 3,3-dimethylbutane-1-sulfonate or a pharmaceutically acceptable salt thereof.

10. A compound according to claim 1 that is ethanesulfonic acid 4-[2-(2,4-dichlorophenyl)-5-methyl-4-(piperidin-1-ylcarbamoyl)-imidazol-1-yl]phenyl ester or a pharmaceutically acceptable salt thereof.

* * * * *